(12) United States Patent
Raman et al.

(10) Patent No.: US 7,379,574 B2
(45) Date of Patent: May 27, 2008

(54) QUANTIFICATION OF VASCULAR IRREGULARITY

(75) Inventors: Raghav Raman, Cupertino, CA (US); Bhargav Raman, San Jose, CA (US); Sandy A. Napel, Menlo Park, CA (US); Geoffrey D. Rubin, Woodside, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 587 days.

(21) Appl. No.: 11/004,630

(22) Filed: Dec. 2, 2004

(65) Prior Publication Data

US 2005/0180621 A1    Aug. 18, 2005

Related U.S. Application Data

(63) Continuation-in-part of application No. 10/722,851, filed on Nov. 26, 2003.

(60) Provisional application No. 60/526,560, filed on Dec. 3, 2003, provisional application No. 60/429,833, filed on Nov. 27, 2002.

(51) Int. Cl.
*G06K 9/00*    (2006.01)
*A61F 2/06*    (2006.01)
*A61B 5/05*    (2006.01)

(52) U.S. Cl. ........................ 382/128; 600/425; 623/1.34

(58) Field of Classification Search ................ 382/128, 382/131; 623/1.24, 1.44, 1.39, 1.46; 128/922; 600/131
See application file for complete search history.

(56) References Cited

U.S. PATENT DOCUMENTS 5,699,799 A * 12/1997 Xu et al. ..................... 600/407
5,755,775 A * 5/1998 Trerotola et al. ............ 606/194
5,881,124 A * 3/1999 Giger et al. ................... 378/8

(Continued)

OTHER PUBLICATIONS

GE Medical System, (2000); Fotey et al; "Application in Pre-stent Graft evaluation and Post-stent Graft Imaging", Medical college of Wisconsin.*

(Continued)

*Primary Examiner*—Joseph Mancuso
*Assistant Examiner*—Nancy Bitar
(74) *Attorney, Agent, or Firm*—Lumen Intellectual Property Services, Inc.

(57) ABSTRACT

A method to quantify the vascular irregularity of aortoiliac arteries is provided. Inner wall and/or outer wall outlines of a vessel of interest are determined. The cross sectional area is determined for the area outlined by each outline. Using this cross sectional area a shape is selected that has substantially the same area as the outline. Subsequently, the shape is fitted to the outline. In one aspect, the irregularity index is calculated as the ratio of the outline and the outline of the fitted shape. In another aspect, the irregularity index is calculated as the ratio of at least a part of the outline and the outline of the fitted shape that corresponds to the same part of the outline. The irregularity index is visualized using a color scheme, a range of numbers, or a set of labels.

9 Claims, 14 Drawing Sheets

U.S. PATENT DOCUMENTS

| | | | | |
|---|---|---|---|---|
| 6,272,370 | B1* | 8/2001 | Gillies et al. | 600/411 |
| 6,728,566 | B1* | 4/2004 | Subramanyan et al. | 600/407 |
| 6,782,284 | B1* | 8/2004 | Subramanyan et al. | 600/407 |
| 6,819,790 | B2* | 11/2004 | Suzuki et al. | 382/156 |
| 2003/0204236 | A1* | 10/2003 | Letort | 623/1.11 |
| 2004/0171932 | A1* | 9/2004 | Raman et al. | 600/425 |
| 2004/0193259 | A1* | 9/2004 | Gabbay | 623/2.11 |
| 2005/0100208 | A1* | 5/2005 | Suzuki et al. | 382/157 |

OTHER PUBLICATIONS

3-D deformable model for abdominal aortic aneurysm segmentation from Ct images, Loncarie et al.(Jun. 14-15, 2000, Pula, Croatia).*

Inter-and Intraobserver Variability of CT measurements obtained after Endovascular Repair of Abdominal Aortic Aneurysms, Wever et al, 2000: 175:1279-1282.*

Volumetric Analysis of Abdominal Aortic Aneurysm, Baskin et al, University of Iowa College of Medicine, 2000.*

Detection of pigment in dermatoscopy images using texture analysis; Murali et al; 2004 Published by Elsevier Ltd.*

Endograft migration one to four years after endovascular abdominal aortic aneurysm repair with the AneuRx device; Conners et al, New Orleans, La, (J Vasc Surg 2002; 36:476-84).*

Prediction of Aortoilliac Stent Graft Length:Comparison of Measurement methods, Tillich et al. Stanford University School of Medicine (2000).*

Tillich etal. (2001) in a paper entitled "Iliac Arterial Injuries After Endovasular repair of Abdominal Aortic Aneurysms: Correlation with Iliac Curvature and Diameter" and published in Radiology 219:129-136.

Hatakeyama et al (2001) in a paper entitled " Risk Factors for Rupture of Abdominal Aortic Aneurysm Based on Three-Dimensional Study" and published in Journal of Vascular Surgery 33(3):453-456.

White et al. (2001) in a paper entitled "Computed Tomography Assessment of Abdominal Aortic Aneurysm Morphology After Endograft Exclusion" and published in Journal of Vascular Surgery 33:S1-10.

Tillich et al. (2001) in a paper entitled "Prediction of Aortoilic Stent-Graft Length: Comparison of Measurement Methods" and published in Vascular and Interventional Radiology 220:475-483.

Ravhon et al. (2001) in a paper entitled "Validation of Ultrasonic Image Boundary Recognition in Abdominal Aortic Aneurysm" and published in IEEE Trans Med Imaging 20(8): 751-763.

Leotta et al. (2001) in a paper entitled "Measurement of Abdominal Aortic Aneurysms with Three-Dimensional Ultrasound Imaging" and published in Prelimary Report, Journal of Vascular Surgery 33(4): 700-707.

Zarins et al. (2001) in a paper entitled " The AneuRx Stent Graft: Four-Year Results and Worldwide Experience" and published in Journal Vascular Surgery 33:S135-145.

Holzenbein et al. (2001) in a paper entitled "Midterm Durability of Abdominal Aortic Aneurysm Endograft Repair: a Word of Caution" and published in Journal Vascular Surgery 33; S46-54.

Makaroun et al. (2001) in a paper entitled "Us Proximal Aortic Neck Dilatation After Endovascular Aneurysm Exlusion a Cause for Concern" and published in Journal Vascular Surgery 33; S39-45.

Baskin et al. (1996) in a paper entitled "Volumetric Analysis of Abdominal Aortic Aneurysm" and published in Medical Imaging: Physiology and Function from Multidimensional Images 2709:323-337.

Wever et al. (2000) in a paper entitled "Inter-and Intraobserver Variability of CT Measurements Obtained After Endovascular Repair of Abdominal Aortic Aneurysms" and published in America Journal of Roentgenology 175: 1279-1282.

Bruijne et al. (2003) in a paper entitled "Model-Based Segmentation of Abdominal Aortic Aneurysms in CTA Images" and published in Medical Imaging vol. 5032: 1560-1571.

Foley et al. (2000) in a paper entitled "Application in Pre-Stent Graft Evaluation and Post-Stent Graft Imaging" and published on www.gehealthcare.com/laes/rad/ct/paf/ava_casestudy_comp.pdf.

* cited by examiner

Figure 7

| *i* | Proximal Neck | Distal Neck | Iliac Arteries |
|---|---|---|---|
| 1 (Normal) | | | |
| 1.01 | | | |
| 1.02 | | | |
| 1.03 | | | |
| 1.04 | | | |
| 1.05 | | | |
| 1.06 | | | |
| 1.06 | | | |
| 1.08 | | | |
| 1.09 | | | |
| 1.10 | | | |
| 1.11 | | | |
| 1.12 | | | |
| 1.13 | | | |
| 1.14 | | | |
| 1.15 | | | |
| 1.16 | | | |
| 1.17 | | | |
| 1.18 | | | |
| 1.19 | | | |
| 1.20 | | | |
| 1.21 | | | |
| 1.22 | | | |
| 1.23 | | | |
| 1.24 | | | |
| 1.25 | | | |
| 1.26 | | | |
| 1.27 | | | |
| 1.28 | | | |
| 1.29 | | | |
| 1.30 | | | |
| (Very Abnormal) | | | |

1010

1110

QUANTIFICATION OF VASCULAR IRREGULARITY

CROSS-REFERENCE TO RELATED APPLICATIONS

This application is a Continuation-In-Part of U.S. Non-Provisional patent application Ser. No. 10/722,851 with filing date of Nov. 26, 2003. This application is cross-referenced to and claims priority from U.S. Non-Provisional patent application Ser. No. 10/722,851 with filing date of Nov. 26, 2003, which claims priority from U.S. Provisional Application 60/429,833 filed Nov. 27, 2002. This application is also cross-referenced to and claims priority from U.S. Provisional Application 60/526,560 filed Dec. 3, 2003. All these applications are hereby incorporated by reference.

STATEMENT REGARDING FEDERALLY SPONSORED RESEARCH OR DEVELOPMENT

The present invention was supported in part by grant numbers 5R01HL58915 and 1R01HL67194 both from the National Institutes of Health (NIH). The U.S. Government has certain rights in the invention.

FIELD OF THE INVENTION

The present invention relates generally to medical imaging. More particularly, the present invention relates to a method for quantifying vascular irregularity.

BACKGROUND

Treatment of abdominal aortic aneurysms (AAAs) with minimally invasive endovascular stent-grafts is gaining wide acceptance (See e.g. Zarins et al. (2001) in a paper entitled "*The AneuRx stent graft: four-year results and worldwide experience*" and published in J Vasc Surg 33:S135-145). However complications related to the breakdown of stent-graft fixation still occur (See e.g. Holzenbein et al. (2001) in a paper entitled "*Midterm durability of abdominal aortic aneurysm endograft repair: a word of caution*" and published in J Vasc Surg 33:S46-54). The characteristics of the intended proximal and distal landing zones (also referred to as attachment sites) of the stent-graft have a significant impact on its long-term stability (See e.g. Makaroun et al. (2001) in a paper entitled "*Is proximal aortic neck dilatation after endovascular aneurysm exclusion a cause for concern?*" and published in J Vasc Surg 33:S39-45). After endovascular repair, aneurysm regression leads to a progressive change in aortoiliac morphology that subjects the attachment sites of the stent-graft prosthesis to angular and torsional stress. Expansion of the proximal neck and distal migration of the device can also occur, promoting the loss of the seal between the stent-graft and the vessel wall. A breakdown of fixation can cause re-perfusion and re-pressurization of the aneurysm sac, thereby increasing the likelihood of aneurysm enlargement or rupture (See e.g. Makaroun et al. (2001) in a paper entitled "*Is proximal aortic neck dilatation after endovascular aneurysm exclusion a cause for concern?*" and published in J Vasc Surg 33:S39-45). Consequently, preoperative assessment of the intended stent-graft attachment sites is routinely performed as a part of the preoperative workup, usually by employing Computed Tomography Angiography (CTA) to quantify the size, length and angulation of the proximal and distal necks of the aneurysm and of the common iliac arteries (See e.g. White et al. (2001) in a paper entitled "*Computed tomography assessment of abdominal aortic aneurysm morphology after endograft exclusion*" and published in J Vasc Surg 33:S1-10).

However, stent-graft attachment would be compromised by excessive irregularity at the attachment sites, for instance due to an incomplete seal possibly causing an endoleak. The present invention advances the art by providing new methods of quantifying vascular irregularity to aid in the assessment of stent-graft surgery.

SUMMARY OF THE INVENTION

The present invention provides a method to quantify the vascular irregularity of aortoiliac arteries. The method could assist in preoperative planning to aid in the assessment of patients before endoluminal stent-graft surgery and could also assist in scheduling postoperative follow-up. The method could be incorporated into standard CT Angiography processing software packages and act as an additional aid in clinical decision-making.

Inner wall and/or outer wall outlines of a vessel of interest are determined. Inner wall outlines are determined using edge detection or adaptive thresholding methods in cross sectional images of a CTA. Outer wall outlines are determined using texture analysis methods in cross section images of a CTA. The inner wall outline follows the flow channel of the vessel and excludes calcium and a mural thrombus. The outer outline follows the mural thrombus of the vessel and includes calcium. The cross sectional area is determined for the area outlined by the inner wall or outer wall. Using this cross sectional area a shape (e.g. a circle, ellipse or a sphere) is selected that has substantially the same area as inner or outer wall outline. Subsequently, the shape is fitted to the inner or outer wall outline using an optimization method such as e.g. a least squares method. In one aspect, the irregularity index is calculated as the ratio of the length of the inner or outer wall outline compared with the length of the respective outline of the fitted shape. In another aspect, the irregularity index is calculated as the ratio of the length of at least a part of the inner wall or outer wall outline to the length of the outline of the fitted shape that corresponds to the same part of the respective outline. In still another variation, the distance of the outline from the corresponding part of the fitted shape can be used to calculate, modify or weigh the measured irregularity. The irregularity index could be visualized or presented using a color scheme, a range of numbers, or a set of labels.

BRIEF DESCRIPTION OF THE FIGURES

The objectives and advantages of the present invention will be understood by reading the following detailed description in conjunction with the drawings listed infra.

FIGS. 5-7 shows examples of different visualizations or presentations of irregularity indices according to the present invention;

DETAILED DESCRIPTION OF THE INVENTION

The present invention is a method for characterizing the vascular (inner and outer) wall irregularity of the infrarenal aorta and common iliac arteries as an aid in assessing proximal and distal stent-graft fixation sites prior to endoluminal repair of an aneurysm. The proximal stent-graft fixation site is, for an infrarenal aneurysm, the interior surface of the aorta between the inferior renal artery and the proximal neck of the aneurysm. The distal fixation site is usually the distal interior surface of the common iliac artery. Even though the present invention is described with respect to an exemplary embodiment related to the infrarenal aorta and common iliac arteries, the present method could also be useful in characterizing a vascular irregularity of any other (normal and diseased) vessel for evaluative or diagnostic purposes.

A. Inner Wall Irregularity

Figure 1:
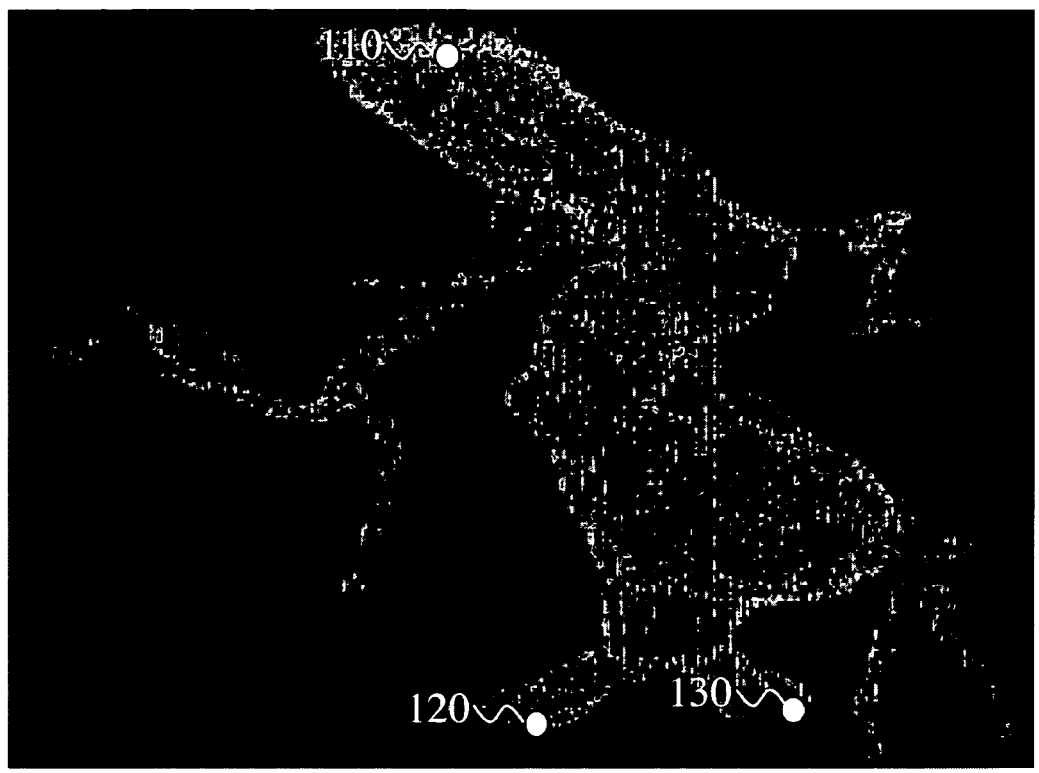
FIG. 1 shows an example of a CTA according to the present invention.
Figure 2:
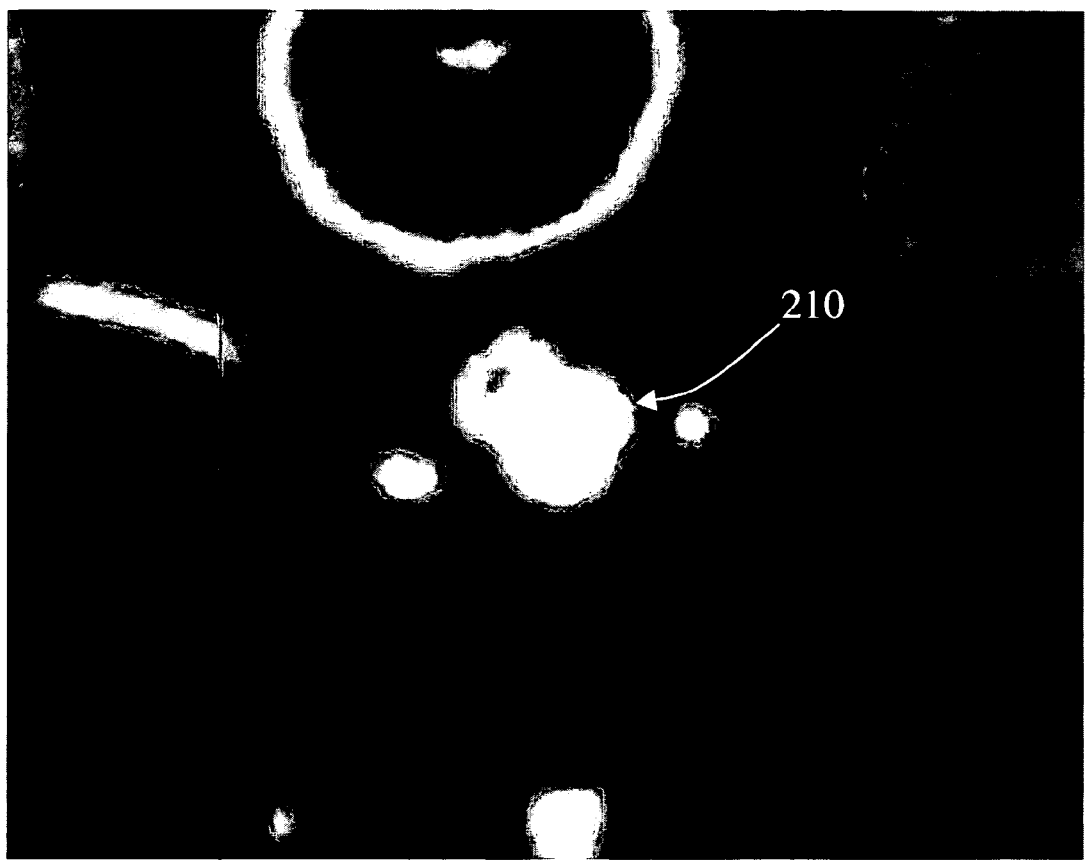
FIG. 2 shows an example of cross sectional view of an aorta according to the present invention.
Figure 3:
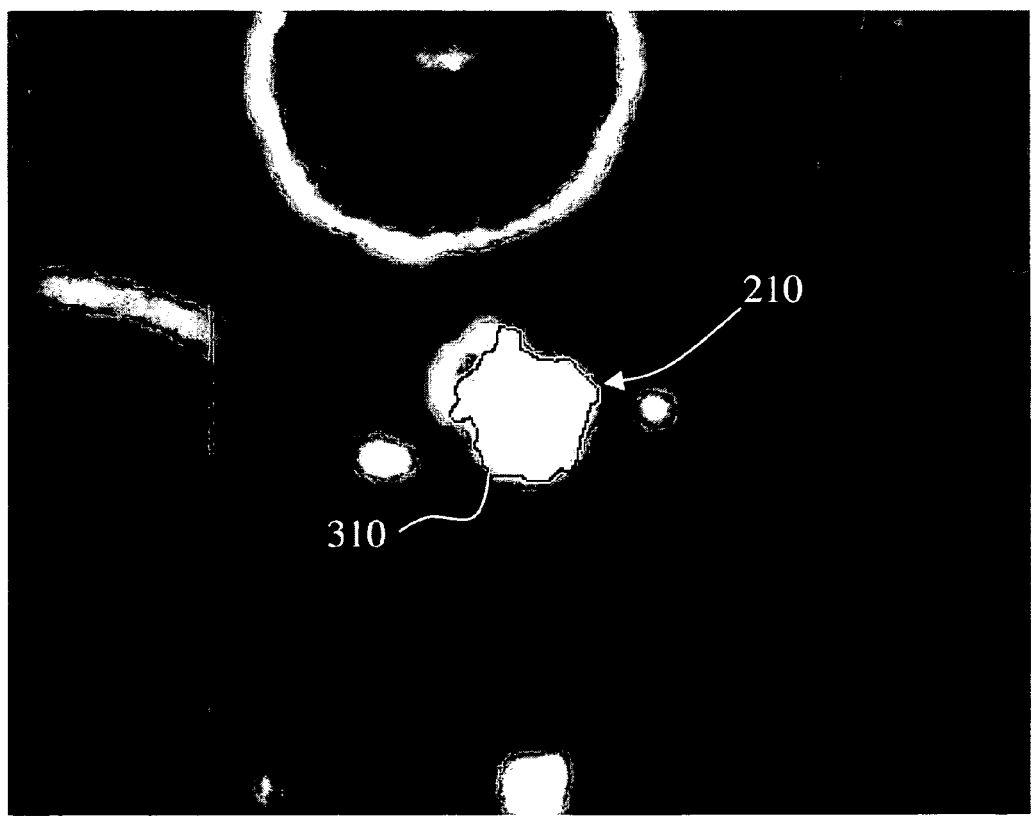
FIG. 3 shows an example of an endoluminal outline according to the present invention.

In one embodiment of the present method a volumetric computed tomography angiography (CTA) dataset is used. To identify the vessel of interest, a user marks two or more points on the CTA. FIG. 1 shows a CTA where three data points are marked on the CTA. One point 110 is marked in the aorta at the inferior real artery (superior to an aneurysm, at the superior extent of the proximal attachment site) and two points 120, 130 at the bifurcation of the common iliac arteries (inferior to the aneurysm, at the distal extent of the distal attachment site). In one aspect of this embodiment, a central path is calculated between these points and perpendicular oblique cross sections of the aorta along its length are extracted. The calculation of the central path is optional, i.e. in case cross sections could be extracted without the centerline calculation, one could omit this step. Cross sections could be obtained at sub-voxel level or at any other level that allows adequate assessment of the radial endoluminal irregularity. FIG. 2 shows an example of a cross section of an aorta 210 for which an irregularity index is determined. The endoluminal outline 310 of this cross section 210 is extracted to only include the flow channel of the vessel. In other words, areas located adjacent to the vessel wall, either inside or outside the vessel wall, which contain calcium or a mural thrombus should not be included in the inner wall vessel outline. The endoluminal outline is typically obtained by edge detection and/or adaptive thresholding, techniques which are common techniques in the art. Optionally the obtained endoluminal outline is smoothed with a filter. Since areas with calcium and a thrombus typically appear with a different intensity in the CTA it is possible to distinguish these from the endoluminal outline. Mural calcium typically has an intensity of 300 Hounsfield Units (HU) or more, while the mural thrombus typically has values between −100 and 100 HU. Values for vessel intensity depend on the amount of contrast material injected prior to the study being done, but usually range from 100 to 300 HU. The next step is to determine the cross sectional area of the area outlines by the endoluminal vessel outline, for instance by integration of the pixels enclosed by the outline. This can be done by performing a scan conversion step that identifies the pixels inside the outline.

Figure 4:
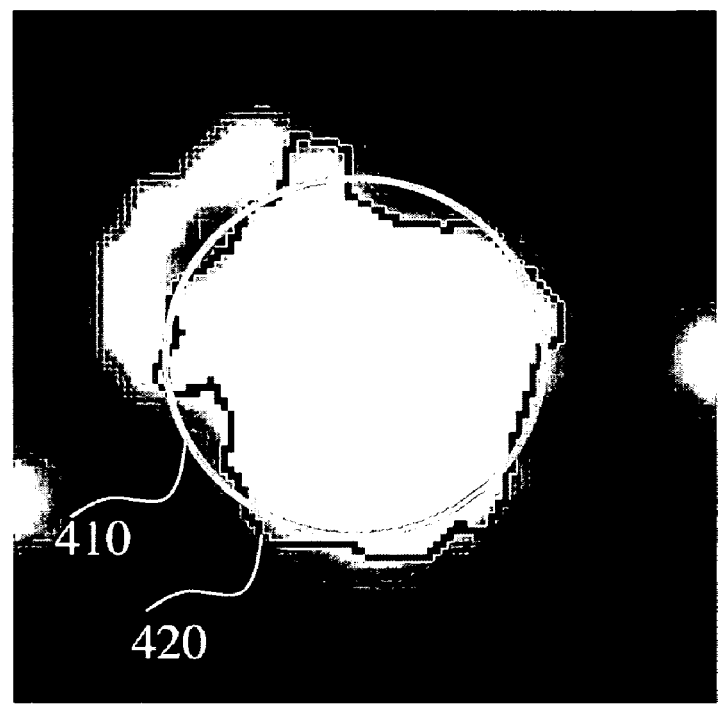
FIG. 4 shows an example of a shape fitted to the endoluminal outline according to the present invention.

Using the determined area of the endoluminal vessel outline, a shape is defined with substantially the same cross sectional area of the one determined for that endoluminal vessel outline. This shape could be preferably a circle, an ellipse or a sphere, however other shapes would also be possible. The selected shape with the same area is now fitted to the endoluminal outline as shown in FIG. 4, for instance, using a least squares method or any optimization method. FIG. 4 shows a circle 410 fitted to outline 420. Note that outline 420 is an enlarged cross section of outline 310.

An irregularity index i is calculated as the ratio of the perimeter of the actual border to the perimeter of the fitted shape with the same cross sectional area as that of the aorta in that image. In general, an irregularity index i could be calculated, not just for the entire perimeter, but also for at least a part (i.e. one or more patches) of the perimeter which then provides an irregularity index for each of those parts (See FIG. 8). The irregularity index is then defined as the ratio of the length of the outline of a selected part of the endoluminal outline to the length of the outline of the fitted shape corresponding to the selected part of the endoluminal outline. The interpretation of the irregularity index is that higher values of i correlate with higher irregularity, since the lowest irregularity for a shape with a given area is attained when that shape is a perfect circle, i.e. 1, in case the selected shape is a circle. It is noted that using this method of an irregularity index standardizes for different cross sectional areas. It is also noted that in one variation, the distance of the endoluminal outline from the corresponding part of the fitted shape can also be used to calculate, modify or weigh the measured irregularity.

Figure 5:
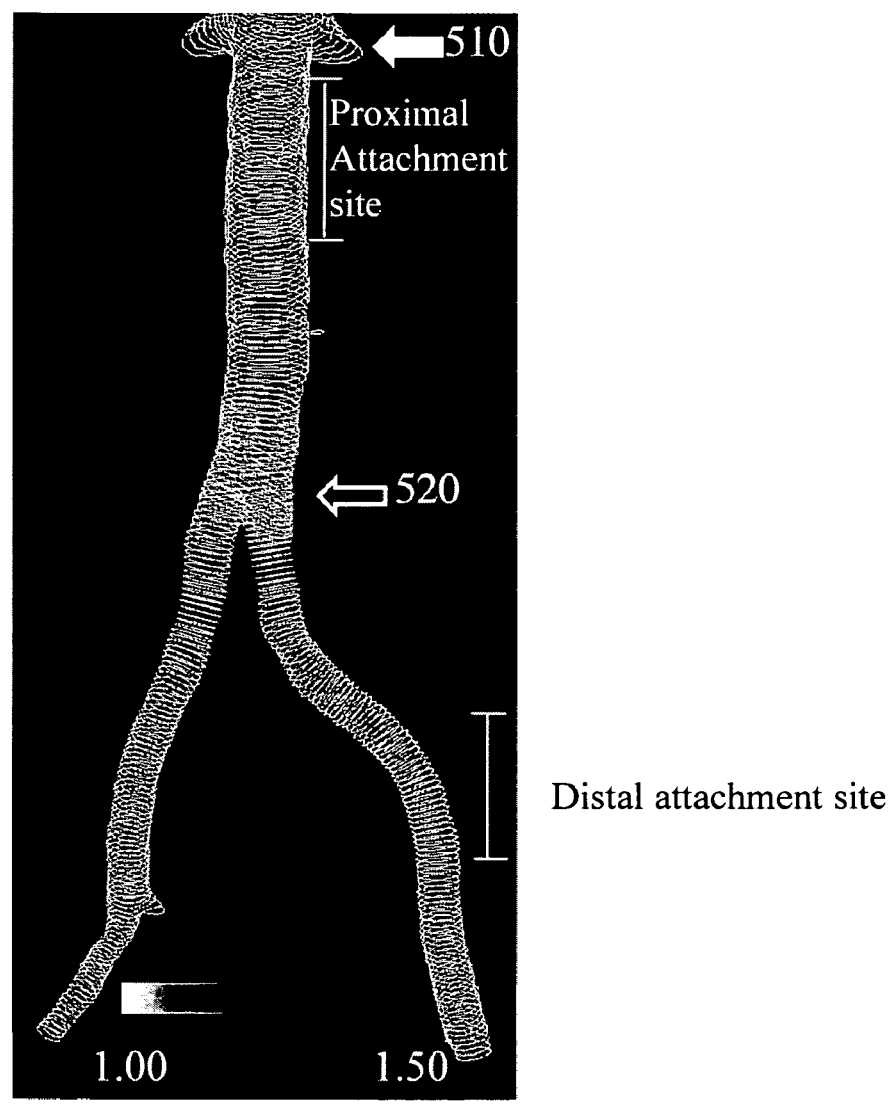
Figure 6:
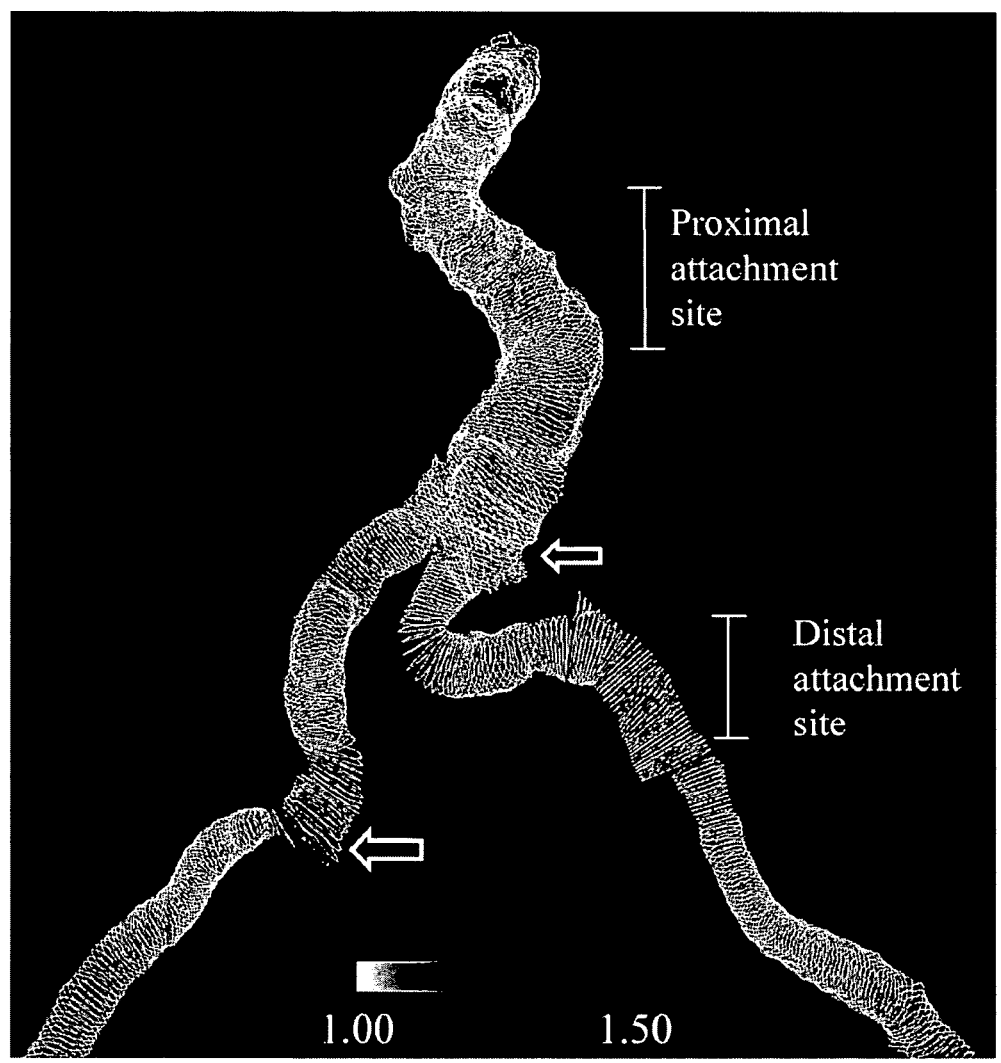
Figure 8:
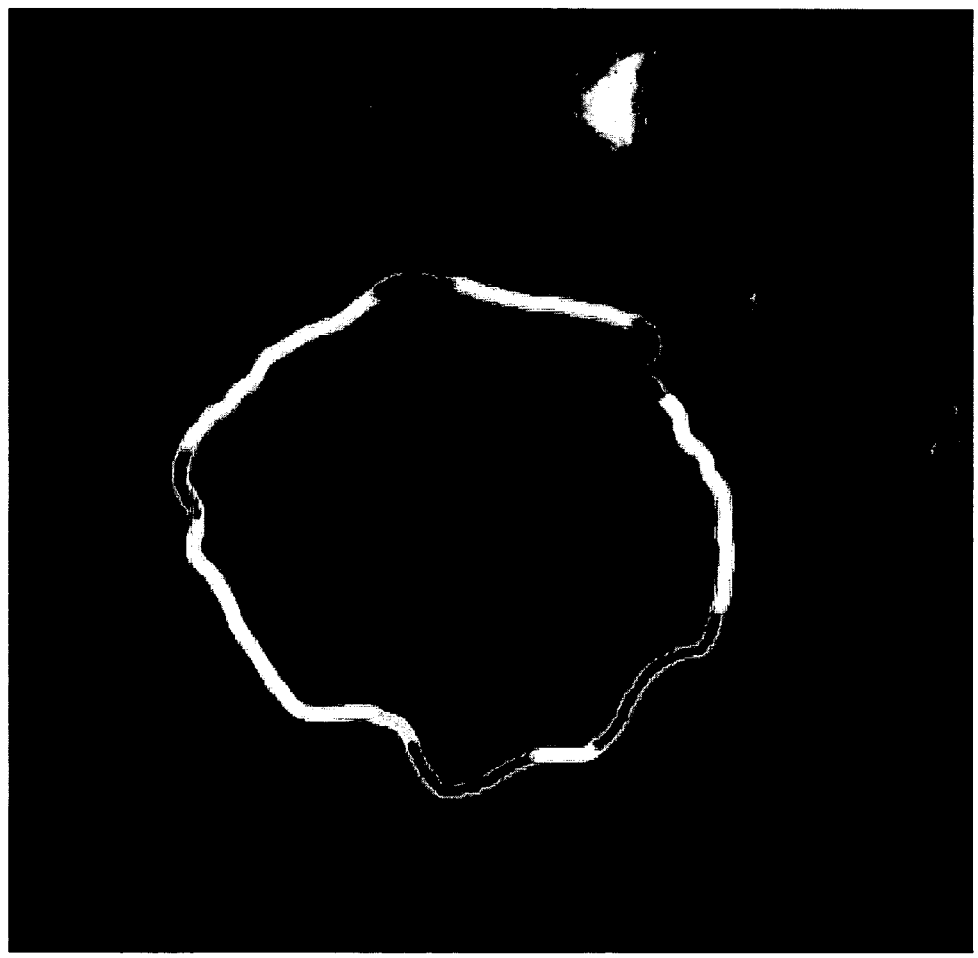
FIG. 8 shows an example of irregularity indices for different part of the endoluminal outline.

The irregularity index could be determined for one cross section but is preferably done for a plurality of cross sections over the length of the selected vessel. In any case, the irregularity index could be visualized or presented using, for instance, but not limited to, a color coding scheme along the vessel, numbers or labels (including fuzzy labels). The visualization of the irregularity index could be done with reference to a range of irregularities encountered in normal patients and in patients with a vascular disease, not limiting to aneurysms. FIGS. 5-8 show different examples of visualization of normal and abnormal vessels with different irregularity indices. FIG. 5 shows a normal aorta with mild irregularity at renal origins (arrow 510) and at the iliac bifurcation (arrow 520). FIG. 6 shows an aneurysmal aorta with irregular proximal and distal stent-graft attachment sites. The distal attachment site had the largest i. The outline arrows show the points where i is artifactually increased at vessel bifurfactions. These areas were not included in the measurements. The irregularity indices in FIGS. 5-6 are shown for each cross section in these images and labeled by a color scheme ranging from green (normal, 1.00) to red (abnormal, 1.50). FIG. 7 shows another way of representing the irregularity index by gray color scheme and numbers for e.g. the proximal neck, distal neck and iliac arteries ranging from normal (ratio of 1) to abnormal levels (ratio larger than 1). FIG. 8 shows an example of different parts (patches) for a vessel outline each with its own irregularity index coded by a color scheme ranging from green (normal), yellow, orange to red (abnormal). These patch irregularities are calculated from the length of the segment and the length of the part of the fitted shape closest to that segment. A weighted average could be employed to calculate the value for a certain patch. Straighter lines will be less irregular than curved lines. The weighting could be accomplished by taking the distance of the endoluminal outline from the corresponding part of the fitted shape.

To validate the present method, we measured irregularity index i in vessel phantoms created using CT simulation/reconstruction software. Phantoms were positioned in the "virtual scanner" at the isocenter and off-isocenter, and scanned longitudinally and transaxially. The image noise in two patient datasets scanned using standard CTA parameters was measured and our simulation software was set to produce, on average, this level of noise in all phantom datasets. The range of vessel sizes and i simulated in phantoms were empirically chosen to include, with a wide margin, the values that would be encountered in the aorta and common iliac arteries. We used three types of phantoms in this validation study. Perfectly regular tapering vessel phantoms with diameters ranging from 2-8 centimeters were used to verify the reliability of measurement in a wide range of vessel sizes. Irregularity was simulated using elliptical vessel phantoms with varying sizes and degrees of eccentricity. Finally, phantoms with continuously varying cross-sectional profiles simulating varying degrees of irregularity were used to approximate the characteristics of vessels in-vivo. Elliptical phantoms had theoretical values of i ranging from 1.00 to 1.60 while phantoms with continuously varying cross-sections simulated a theoretical i of 1.00 to 1.40. Centerlines were obtained through CT reconstructions of these simulated phantoms and measurements of i were compared to the known values using linear regression.

As a result, in regular vessel phantoms, the average measured i was 1.02±0.01, corresponding to a fractional error of measurement of 2±1%. In phantoms simulating irregular vessels, the fractional error in measurement of i was 2±3%, with $R^2=0.973$ ($p<0.001$). The maximal error encountered was an overestimation of i by 11.4%. This occurred in the longitudinal scan of phantoms with the smallest diameter studied (2 centimeters).

To demonstrate the irregularity index measurements in patient datasets, we obtained abdominal aortoiliac CTAs of 5 normal and 15 abnormal patients (13 male, 7 female, mean age 68) with infrarenal AAAs. These patients had their examinations as part of their clinical workup and were chosen consecutively. Measurements of i were made in the anticipated proximal and distal landing zones (aneurysm necks) of an aortoiliac stent-graft (the aorta below renal artery origins to the aneurysm origin and the aorta distal to aneurysm terminus including the entire common iliac arteries respectively) and compared to i measured in the corresponding regions of patients without aneurysms.

As a result, the diameter of the infrarenal aorta and common iliac arteries in patients without aortoiliac disease was 18.9±0.8 mm and 9.7±1.8 mm. The diameter of proximal necks, distal necks and common iliac arteries in abnormal patients was 20.3±2.7 mm, 24.6±2.4 and 15.9±2.7 respectively. In patients without aortoiliac disease, the mean i of proximal and distal infrarenal aorta was 1.05 (95% CI 1.04, 1.06) and 1.06 (95% CI 1.05, 1.06) respectively while in patients with AAAs, the mean i of proximal and distal aneurysm necks was 1.21 (95% CI 1.12, 1.30) and 1.26 (95% CI 1.21, 1.31) respectively. The mean i of normal common iliac arteries was 1.04 (95% CI 1.01, 1.06). The mean i was 1.12 (95% CI 1.08, 1.16) in those with AAAs. The difference between measurements in normal and abnormal patients was statistically significant for each region ($p<0.01$) and overall ($p<0.01$).

B. Outer Wall Irregularity

Vascular mural thrombus is a common occurrence in the setting of vascular disease. Mural thrombus is defined as coagulated blood in the lumen of a vessel, or contained within or surrounding the wall of the vessel. It occurs most commonly in the setting of atherosclerotic vascular disease, but can occur wherever there is turbulent flow, stasis, local or systemic hypercoagulability or vessel wall damage.

Figure 9:
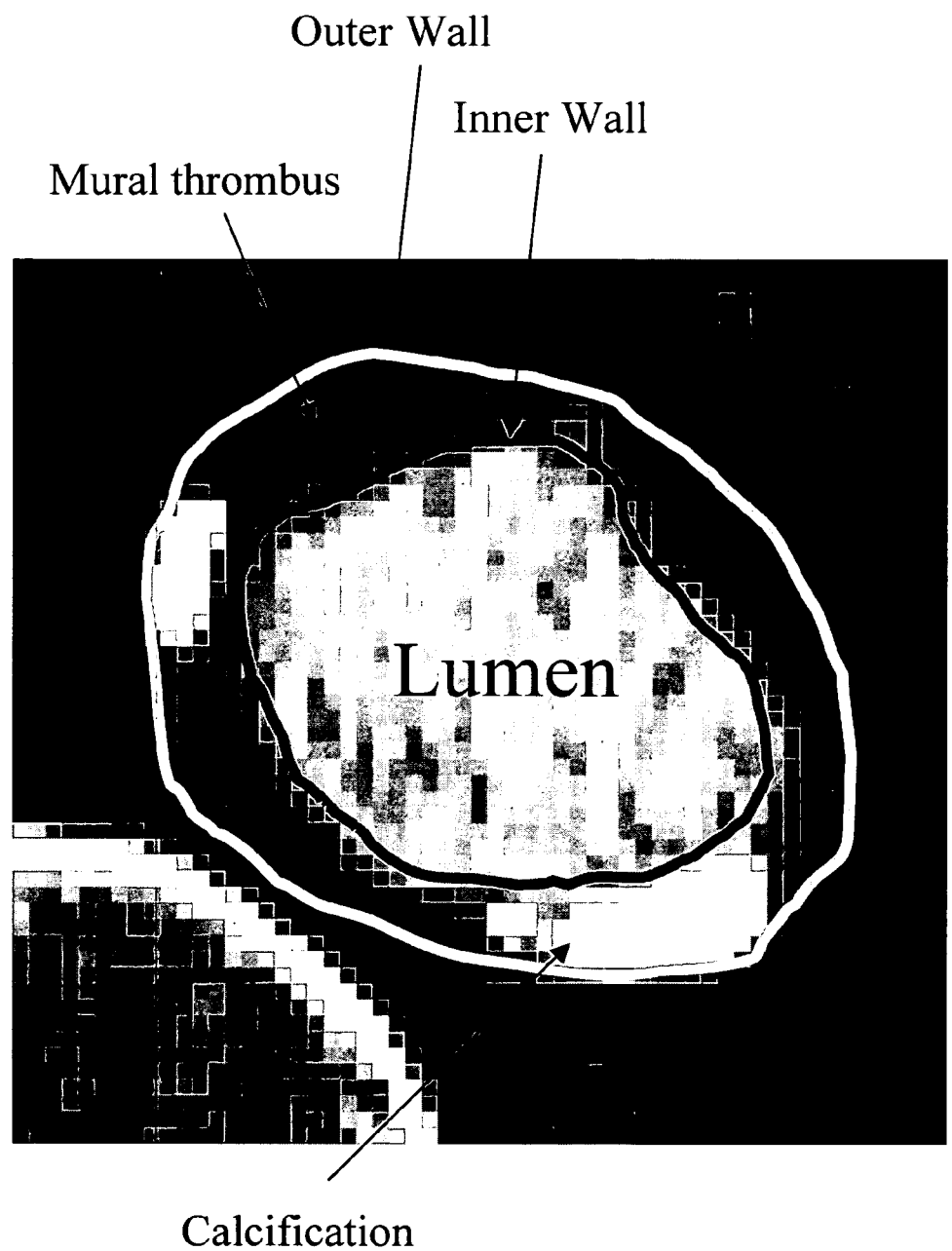
FIG. 9 shows an example of an inner wall outline and an outer wall outline.

In the management of atherosclerotic and other vascular disease, the quantity and distribution of mural thrombus is an important factor in localizing disease and in deciding management. For example, in the setting of aortic aneurysm management, the true size of the aneurysm (patent lumen+ surrounding thrombus) dictates the urgency of management (See FIG. 9). In determining the total volume and diameters of the aneurysm, both the lumen and the surrounding thrombus should be included. In describing the morphology of the aneurysm, the shape of the aneurysm sac is defined by the outer borders of the thrombus (outer wall). The presence of high contrast streaks in the thrombus is a harbinger of impending rupture. When evaluating a patient for an endovascular stent-graft, the amount of thrombus proximal and distal to the aneurysm correlates with poor fixation of the proximal and distal ends of the graft, leading to postoperative graft migration and type I endoleaks.

In patients being screened for atherosclerotic disease using CT scans, the presence of mural thrombus is one factor that localizes atherosclerotic disease. As described in section A, supra, irregularity of the vessel lumen also localizes vessel wall disease.

The quantification of mural thrombus is problematic. The intensity of mural thrombus is very close to that of surrounding tissues and fat. Due to differences in scanning protocol, image noise and thrombus composition, the intensity and texture of thrombus is (very) variable between patients. The margin between contrast-filled patent vessel lumen and the mural thrombus is (very) distinct due to the large contrast difference between vessel lumen and thrombus, and the thrombus is always of lower intensity when compared to vessel lumen. However, the soft tissue surrounding the mural thrombus could be of higher, lower or similar intensity to the mural thrombus. In other words, there is usually a recognizable difference between the texture of thrombus and that of surrounding tissue.

Figure 10:
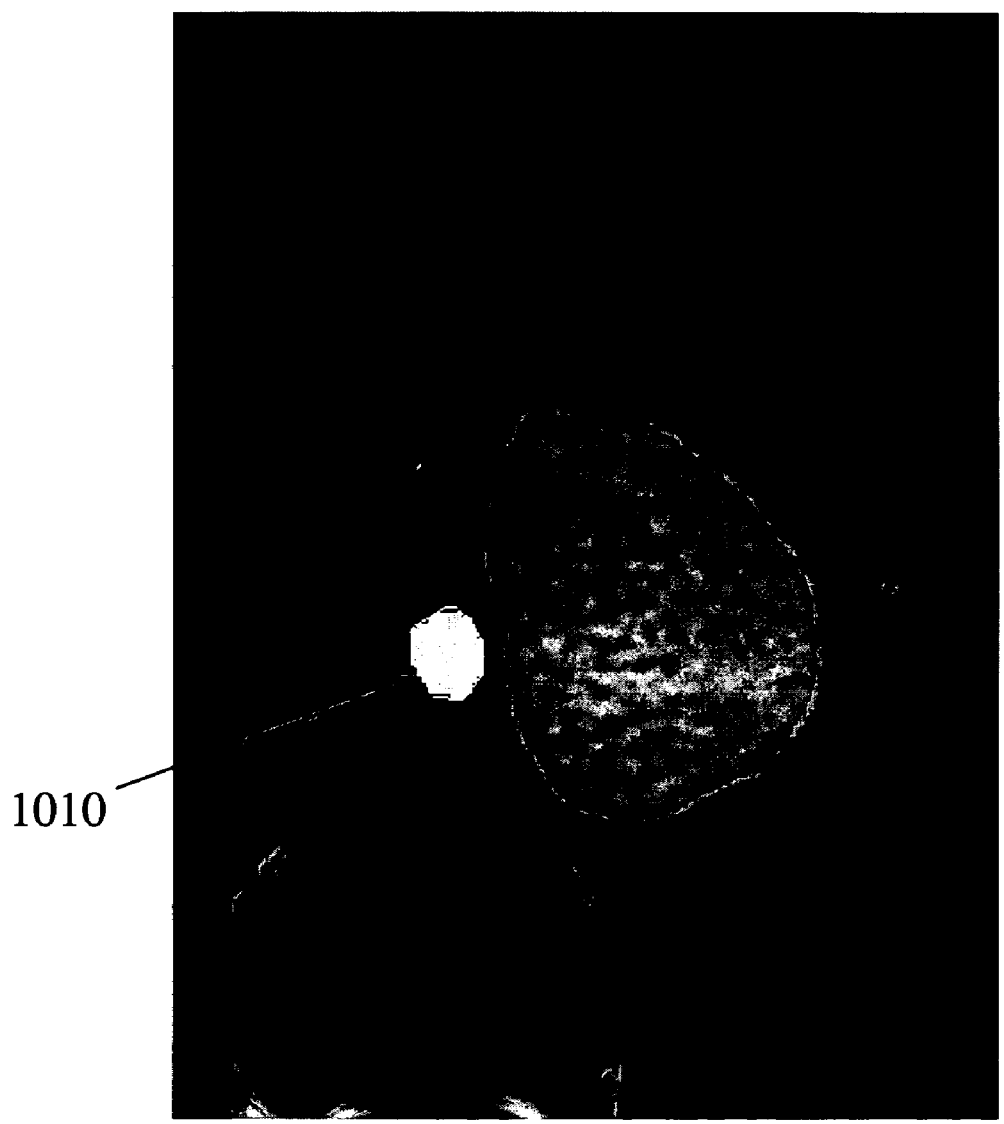
FIG. 10 shows an example of a reference thrombus sample.
Figure 11:
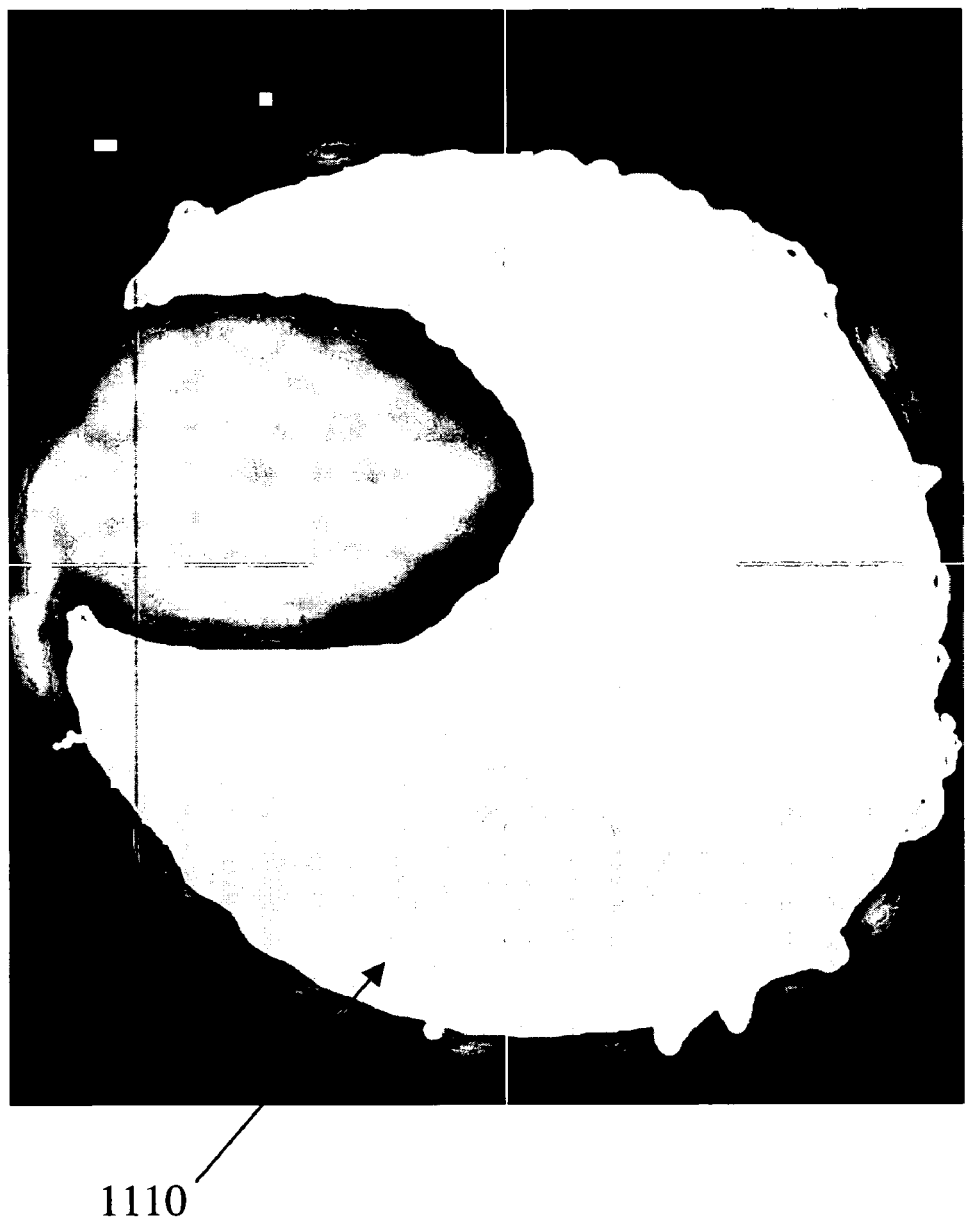
FIG. 11 shows an example of an output 1110 of thrombus texture analysis based on the reference thrombus sample.
Figure 12:
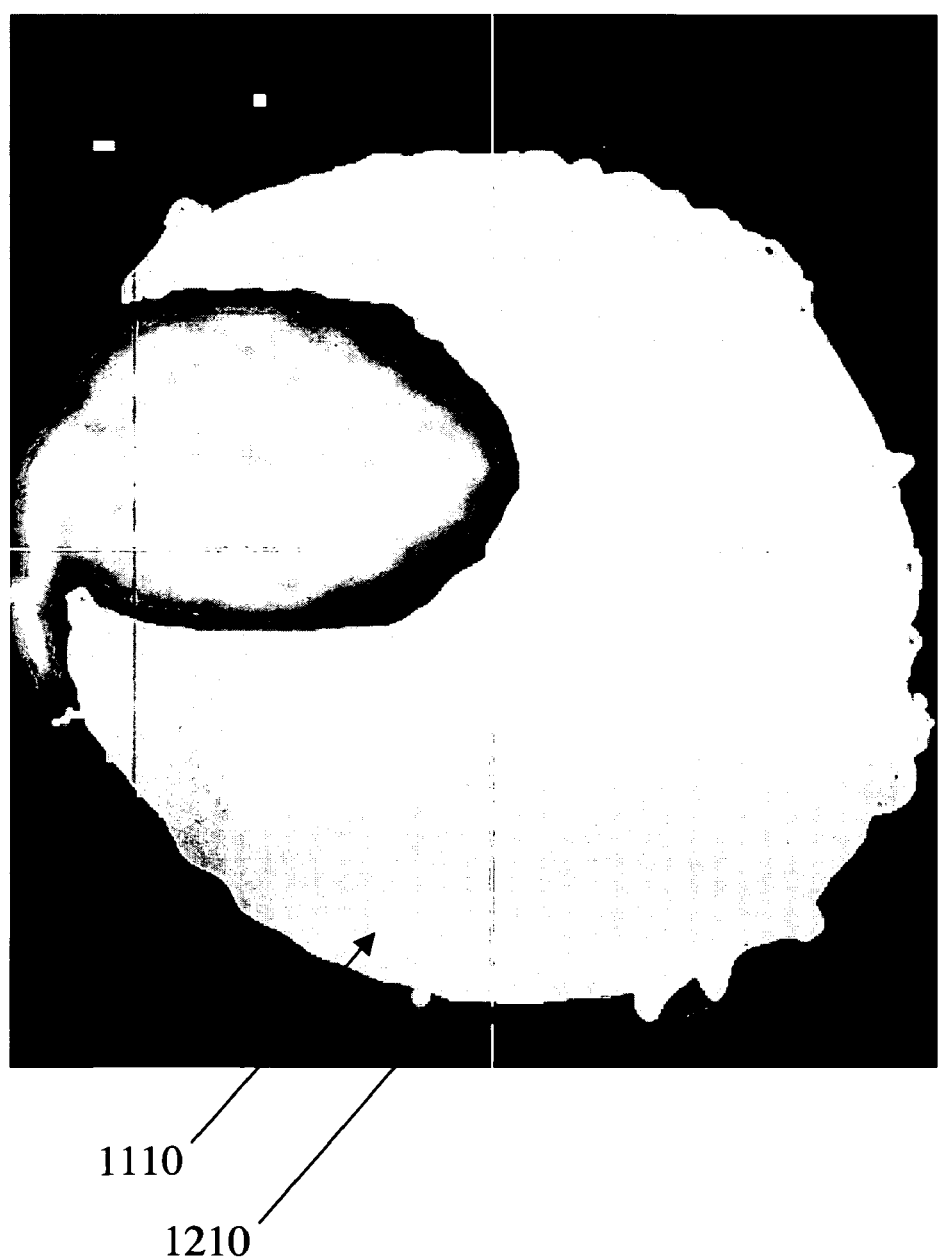
FIG. 12 shows the same output as in FIG. 11 with the addition of identified calcium 1210.
Figure 13:
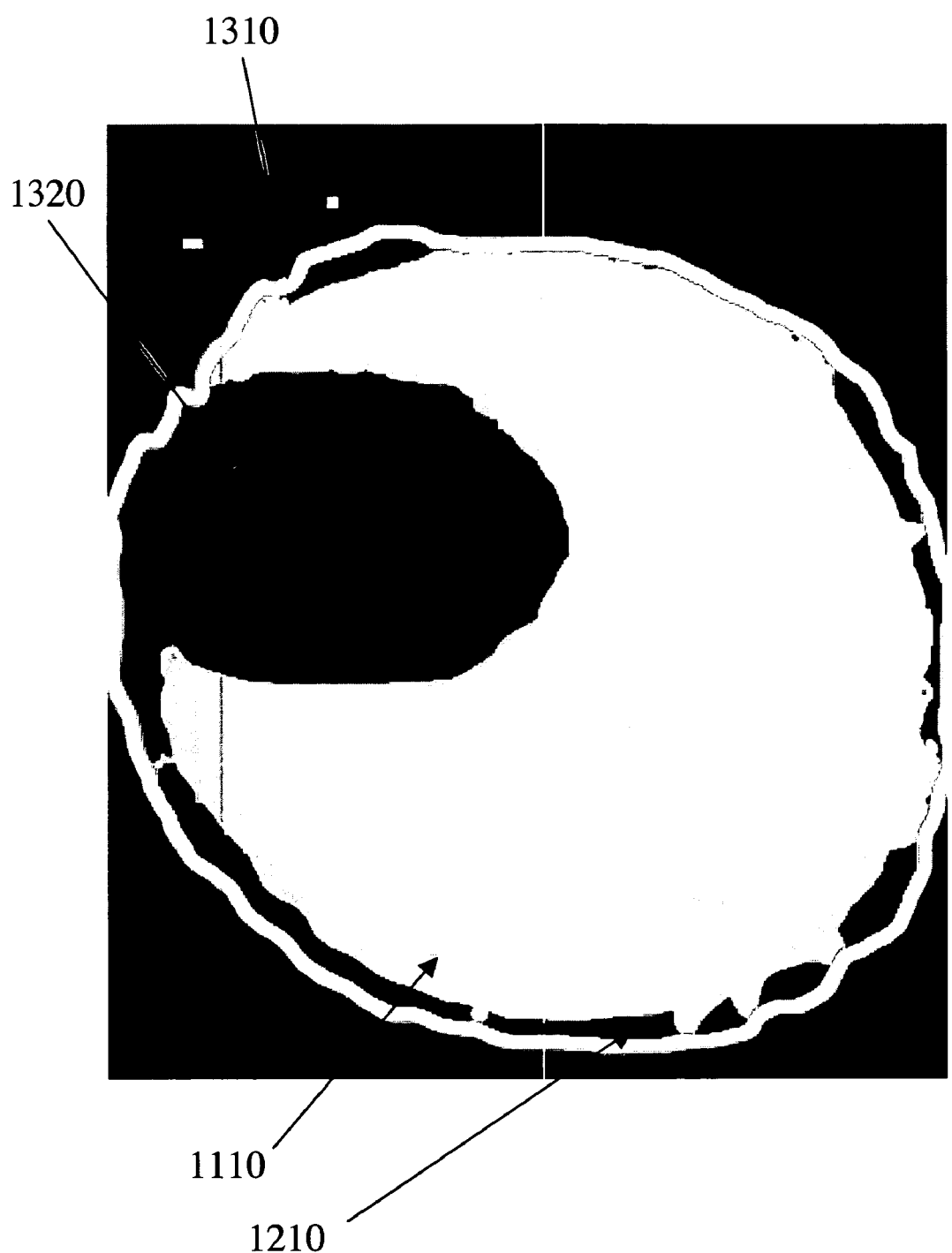
FIG. 13 shows an example of the outer wall 1310, inner lumen 1320 and calcium 1330.
Figure 14:
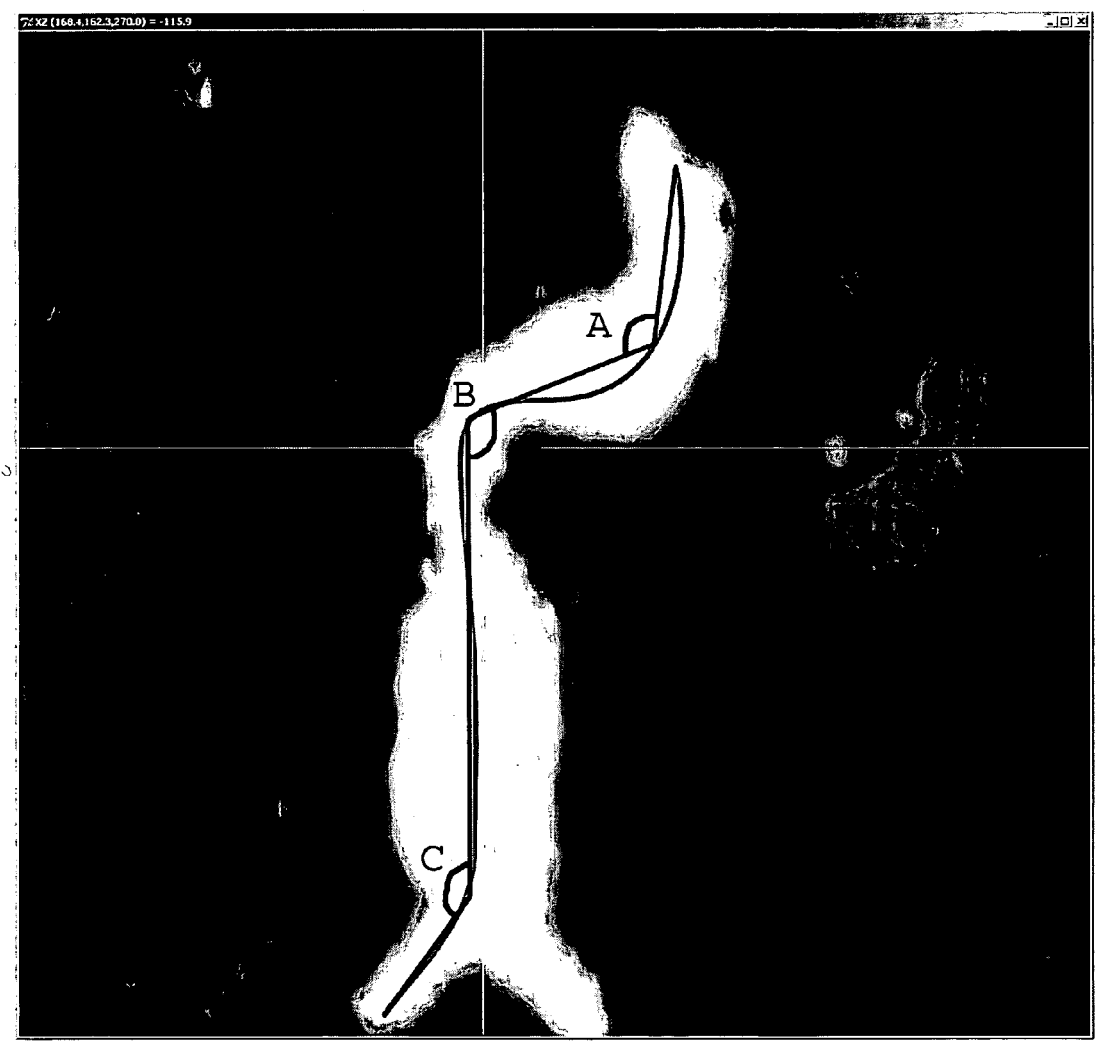
FIG. 14 shows an example of angles of a vessel course.

The present invention further includes a method that identifies and quantifies mural thrombus using multiscale three dimensional texture analysis. Firstly, it uses a small sample 1010 of identified thrombus in an image of a patient as a model to identify all other thrombus in the patient's vessels (See FIG. 10). This initial reference sample can be identified in many ways. In the setting of an aortic aneurysm, a small piece of tissue adjacent to the patent vessel lumen at the midpoint of the aneurysm is automatically chosen as a model region. In patients with highly irregular thrombus distribution, the user can manually highlight a small portion of representative thrombus. This way, the method compensates for the wide variation in thrombus texture between patients.

For this sample volume, statistical descriptors are calculated to characterize the sample thrombus. These descriptors are calculated for the following kernel sizes (X,Y,Z) 2×2×2, 3×3×2, 3×3×3, 4×4×2, 4×4×3, 4×4×4 voxels. These kernel sizes were chosen because most CT scans have a higher resolution in-plane (x and y axes) and have a lower resolution through plane (z axis). Therefore, the kernel sizes chosen are weighted towards the x and y axes. For the voxels included in each kernel, the following descriptors are calculated: Mean intensity, standard deviation ($2^{nd}$ moment about the mean), skewness ($3^{rd}$ moment), kurtosis ($4^{th}$ moment), ratio of high to low intensity voxels (where low intensity is defines as voxels with an intensity less than water at 0 Hounsfield units), the mean and standard deviation of distance of high intensity voxels from the kernel center and the mean and standard deviation of distance of low intensity voxels from the kernel center. In addition, each connected group of high and low intensity voxels in each kernel was extracted and the following descriptors were calculated: number of high and low intensity groups, mean distance of each high intensity group to the nearest high intensity group, mean distance of each low intensity group to the nearest low intensity group, mean distance of each high intensity group to the nearest low intensity group.

For each of these descriptors or a subset of these descriptors, the mean and standard deviation of descriptor values in the sample is calculated. Confidence intervals are generated for each descriptor value, such that a theoretical 95% of the patient's thrombus tissue will have descriptor values within that confidence interval. From the operation of the method to quantify the irregularity of the vessel lumen (inner wall) as described supra, the boundaries of the vessel lumen are already available. All tissue within about 10 centimeters of the lumen boundary is then evaluated for thrombus as follows: Firstly the statistical descriptors are calculated for each voxel in this candidate volume. For each voxel, a thrombus probability value is calculated for each kernel based on the proportion of statistical descriptors that fall within the 95% confidence intervals of the sample volume. The probability can be calculated as being equivalent to the proportion, but in an alternative embodiment the higher order/higher moment statistical descriptors are weighted higher, in proportion to their complexity. Then the probability values for each kernel are averaged. A weighting factor can be applied when the probabilities are averaged. The highest weight is applied to the kernel with the largest x-y size since this kernel has the highest likelihood of capturing useful texture information (i.e. 4×4×4) and the smallest weight is given to the smallest kernel (2×2×2) with medium weights given to the other kernels. Note that all statistical descriptors used for this algorithm are direction-independent. There is no directionality for thrombus formation, and thrombus textures are randomly oriented in three dimensions. Hence directional textures, which are very useful for example to describe complex biological structures such as wood grains, are inappropriate for pathological thrombus identification.

As with any statistical process, the tissues identified have false positives and false negatives. For example, small volumes of tissue actually in the bowel surrounding the aneurysm are sometimes identified as possible thrombus. These tissues usually have a lower thrombus probability value assigned to them. Firstly, tissue with a <90% probability of being thrombus is excluded. This step would only retain tissue with high probability of being thrombus (high specificity) but would miss some tissue that was really thrombus (low sensitivity).

As a further step, the method uses a cost function to discard tissues that are not likely to be part of the vessel wall and include thrombus in the vessel wall that was excluded in the previous step. The cost function is designed to extract a contiguous vessel outer wall that includes the high-probability thrombus tissue as well as other thrombus tissue that was previously excluded. It also encloses the inner lumen that was previously identified.

Therefore, the outer wall boundary will include tissue that was previously excluded because of a low probability of being thrombus. This would include erroneous false negatives (thrombus that was excluded), as well as calcium in the vessel wall.

However, calcium located at the margin of the thrombus is not included in this initial outer wall boundary, since there is no thrombus on the outer edge of this calcium. Therefore, all high intensity fragments <150 voxels in size that are in direct contact with the initial outer wall boundary is included, and the boundary is expanded to encompass these fragments.

Once the outer wall boundary is extracted as described, the irregularity of the outer wall can then be quantified and visualized in an identical fashion as for the inner wall as described in Section A supra. In addition, the true average diameter and total volume of the aneurysm can be calculated from the volume enclosed by the outer wall boundary.

C. Vessel Angles

In a further enhancement to the present method, the identified inner and outer boundaries of the vessel can be used to calculate the "principal angulations" of the vessel course. This enhancement allows a more complete analysis of the vessel irregularity, since vessel irregularity is often associated with vessel tortuosity. Previous methods in the art of calculating angulation of vessels relied mostly on determining the angle between branches of vessels, or angles along the vessel at specified, manually selected landmark points. Here in the present method we take a different approach that does not require any landmarks and depicts the most important angulations possessed by a vessel. Firstly, the volume enclosed by the boundary is used to generate a centerline path through the vessel. Many known methods can be used to extract this centerline. Once the centerline is extracted, the following method steps are applied to determine the principal angulations.

Firstly, the origin of the vessel under analysis is selected as the origin point for angle measurements, and the termination of the vessel is selected as the termination point for angle measurements. Initially, two consecutive line segments are drawn between the origin point, one of the intermediate points on the centerline, and the termination point. The length of these two line segments is compared to the length of the centerline itself. The fit of the line segments to the centerline is calculated as the percentage difference between the longer centerline and the shorter length of the two line segments combined. This process is repeated by selecting every intermediate point on the centerline as the intermediate point for the 2 line segments. If none of these combinations produce a fit greater than 95% then the process is repeated with three line segments and two intermediate points. The fit of every possible combination of two intermediate points is then calculated, with the restriction that the second intermediate point always has to be distal on the centerline to the first intermediate point. If none of these combinations produce a fit >95% the process is repeated with more line segments until a satisfactory fit is achieved.

Accordingly, the minimum required number of line segments represents the vessel course and the number of principal angulations the vessel possesses. The values of the angles between the line segments represents the severity of the principal angulations. These values could be used as additional irregularity parameters either separate or in combination with the irregularity parameter(s) or index(indices)

of the inner wall outline or outer wall outline. When these values are applied to the inner boundary, these values (number of line segments and angle values) could be used to assess the patient for suitability for stent graft surgery. When these values are applied to the outer boundary, the values represent the amount of inherent angulation present in the vessel as a whole, and could be used to follow the patient with serial scans to assess the need for surgery. Acute increases in angulation between scans could indicate worsening of the aneurysm. Since aneurysms elongate and tort over time, the use of the number and severity of principal angulations provides a way of assessing the progression of angulation of the vessel as a whole rather than just at landmark points or branch points. However, as a modification to the present method, the principal angulations of part of a vessel between two manually identified anatomic landmark points could be determined if desired. In that case, the origin and termination points would be set as the landmark points identified, rather than the origin and termination of the whole vessel.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations and other variations are considered to be within the scope and spirit of the present invention as defined by the following claims and their legal equivalents.

What is claimed is:

1. A method for characterizing vascular irregularity of a vessel, comprising the steps of:
    (a) determining an outline of said vessel in a cross sectional image, wherein said outline represents the inner wall of said vessel encompassing the vessel lumen or said outline represents the outer wall of said vessel encompassing mural thrombus;
    (b) determine an area of said outline;
    (c) defining a shape with substantially the same area as said outline;
    (d) fitting said shape to said outline;
    (e) calculating an irregularity index which is the ratio of at least a part of said outline and the outline of said fitted shape corresponding to said at least a part of said outline; and
    (f) visualizing said irregularity index.

2. The method as set forth in claim 1, wherein said step of determining said inner wall outline comprises the step of using edge detection or adaptive thresholding or filtering.

3. The method as set forth in claim 1, wherein said step of determining said outer wall outline comprises the step of using texture analysis.

4. The method as set forth in claim 1, wherein said shape is a circle, an ellipse or a sphere.

5. The method as set forth in claim 1, wherein said visualization comprises colors, numbers or labels.

6. The method as set forth in claim 1, wherein said visualization is done with reference to a range of irregularities encountered in normal patients and in patients with a vascular disease.

7. The method as set forth in claim 1, further comprising the step of modifying said irregularity index by the distance of said outline from said corresponding part of said fitted shape.

8. The method as set forth in claim 1, wherein said outline determination is repeated over multiple cross sectional images generating inner wall outlines or outer wall outlines which are used to determine a minimum number of angles of the vessel course.

9. The method as set forth in claim 8, wherein irregularity parameters are determined from said angles.

* * * * *